(12) United States Patent
Wood et al.

(10) Patent No.: US 9,125,761 B2
(45) Date of Patent: Sep. 8, 2015

(54) ENDOSCOPE WITH PRELOADED OR PRELOADABLE STENT

(75) Inventors: Mark D. Wood, Shrewsbury, MA (US); F. Anthony Headley, Jr., Plymouth, MN (US); Gary J. Leanna, Holden, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1397 days.

(21) Appl. No.: 11/861,565

(22) Filed: Sep. 26, 2007

(65) Prior Publication Data

US 2008/0183272 A1   Jul. 31, 2008

Related U.S. Application Data

(60) Provisional application No. 60/897,382, filed on Jan. 25, 2007.

(51) Int. Cl.
*A61F 2/95* (2013.01)
*A61F 2/966* (2013.01)

(52) U.S. Cl.
CPC . *A61F 2/95* (2013.01); *A61F 2/966* (2013.01); *A61F 2002/9511* (2013.01); *A61F 2002/9522* (2013.01)

(58) Field of Classification Search
CPC .............. A61F 2/95; A61F 2002/9522; A61F 2002/9505; A61F 2/966; A61B 1/018
USPC ........ 623/1.11, 1.13, 1.23; 600/104, 123, 153
See application file for complete search history.

(56) References Cited

U.S. PATENT DOCUMENTS

| | | | |
|---|---|---|---|
| 4,911,148 A * | 3/1990 | Sosnowski et al. | 600/136 |
| 5,026,377 A | 6/1991 | Burton et al. | |
| 5,224,953 A * | 7/1993 | Morgentaler | 606/192 |
| 5,921,952 A * | 7/1999 | Desmond, III et al. | 604/8 |
| 5,957,974 A | 9/1999 | Thompson et al. | |
| 6,033,413 A | 3/2000 | Mikus et al. | |
| 6,093,194 A | 7/2000 | Mikus et al. | |
| 6,146,389 A | 11/2000 | Geitz | |

(Continued)

FOREIGN PATENT DOCUMENTS

| WO | 9949812 | 10/1999 |
|---|---|---|
| WO | 02056798 | 7/2002 |

(Continued)

OTHER PUBLICATIONS

Communication pursuant to Article 94(3) EPC issued Jan. 13, 2015 for EP Application No. 07843208.5-1651.

*Primary Examiner* — Katherine Rodjom
(74) *Attorney, Agent, or Firm* — Seager, Tufte & Wickhem LLP (57) ABSTRACT

The present invention is directed to an endoscopic stent delivery device. The device includes an endoscope having an elongate shaft including a proximal end, a distal end, an outer wall and a longitudinal working channel through the elongate shaft defining an inner wall of the elongate shaft; a stent juxtaposingly disposed to a distal portion of the inner wall; and an inner tubular member slidably disposed within the working channel and having a stent holding member engaging an interior portion of the stent for releasably securing the stent to the distal portion of the inner wall. The device may further include a viewing device disposed at the distal end of the endoscope and/or an illuminating device disposed at the distal end of the endoscope.

22 Claims, 8 Drawing Sheets

(56) References Cited

U.S. PATENT DOCUMENTS

| | | | |
|---|---|---|---|
| 6,162,231 A | 12/2000 | Mikus et al. | |
| 6,176,873 B1 | 1/2001 | Ouchi | |
| 6,251,132 B1 | 6/2001 | Ravenscroft et al. | |
| 6,520,983 B1 * | 2/2003 | Colgan et al. | 623/1.11 |
| 6,620,570 B2 | 9/2003 | Kimoto et al. | |
| 6,709,455 B1 * | 3/2004 | Chouinard | 623/1.32 |
| 6,902,575 B2 * | 6/2005 | Laakso et al. | 623/1.11 |
| 6,996,952 B2 * | 2/2006 | Gupta et al. | 53/434 |
| 2002/0087186 A1 * | 7/2002 | Shelso | 606/198 |
| 2002/0143387 A1 | 10/2002 | Soetikno et al. | |
| 2003/0225445 A1 | 12/2003 | Derus et al. | |
| 2004/0098105 A1 | 5/2004 | Stinson et al. | |
| 2005/0085892 A1 * | 4/2005 | Goto et al. | 623/1.12 |
| 2005/0090889 A1 * | 4/2005 | Yanuma et al. | 623/1.11 |
| 2005/0119722 A1 * | 6/2005 | Styrc et al. | 623/1.12 |
| 2005/0125050 A1 * | 6/2005 | Carter et al. | 623/1.11 |
| 2006/0004305 A1 | 1/2006 | George et al. | |
| 2006/0004436 A1 * | 1/2006 | Amarant et al. | 623/1.15 |
| 2006/0184224 A1 | 8/2006 | Angel | |
| 2006/0224235 A1 * | 10/2006 | Rucker | 623/1.21 |
| 2007/0123971 A1 * | 5/2007 | Kennedy et al. | 623/1.11 |
| 2009/0054875 A1 * | 2/2009 | Strauss et al. | 604/528 |

FOREIGN PATENT DOCUMENTS

| | | |
|---|---|---|
| WO | 2005073091 A2 | 8/2005 |
| WO | WO 2005/122953 | 12/2005 |

* cited by examiner

ENDOSCOPE WITH PRELOADED OR PRELOADABLE STENT

CROSS-REFERENCE TO RELATED APPLICATIONS

This application claims the benefit of U.S. Provisional Application No. 60/897,382, filed Jan. 25, 2007, the content of which is incorporated herein by reference.

FIELD OF THE INVENTION

This invention relates to a system and method for endoscopic deliver of a stent. More particularly, this invention relates to an endoscope having a preloaded or preloadable stent, including a radially distensible, polymeric and/or non-polymeric stent.

BACKGROUND OF THE INVENTION

An intraluminary stent is a medical device used in the treatment of diseased bodily lumens, such as in the coronary or peripheral vasculature, esophagus, trachea, bronchi colon, biliary tract, urinary tract, prostate, brain, as well as in a variety of other applications in the body. Contemporary endoscopy practitioners increasingly often require visualization of the damaged vessel while delivering the stent. In some cases an endoscope and a stent delivery catheter are separately advanced to the damaged vessel to allow for visualization of the delivery of the stent from the stent delivery catheter. Such a procedure has size limitation, especially for smaller bodily lumens, as both the endoscope and the stent delivery catheter must be navigated to the damaged vessel.

To avoid the need or disadvantage of intraluminally advancing two separate and independent devices, endoscopes and stent delivery systems have been combined. One technique may have a stent disposed within a stent delivery catheter and an endoscope which is slidable within an inner tube of the catheter. For example, U.S. Patent Application Publication No. 2006/0184224 A1 to Angel and U.S. Pat. No. 6,033,413 to Mikus et al. describe stent delivery systems having a catheter holding a stent between two tubes of the catheter and an endoscope being positioned within the inner shaft of the catheter. The combining of a stent delivery catheter and an endoscope in such a manner, however, limits the diameter of the contracted or loaded stent to a diameter larger than that of the endoscope. In other words, the overall profile of the delivery system is constrained by the size of the endoscope.

Another technique used to avoid the need for separately advancing independent endoscopes and stent delivery catheters, is to have a stent constrained within a stent delivery catheter where the stent delivery catheter is slidably disposed within a lumen of the endoscope. For example, U.S. Patent Application Publication Nos. 2002/0143387 A1 to Soetikno et al.; 2004/0098105 A1 to Stinson et al.; 2005/0090889 A1 to Yanuma et al. and 2005/0125050 A1 to Carter et al. and U.S. Pat. No. 6,162,231 Mikus et al.; U.S. Pat. No. 6,093,194 to Mikus et al. and U.S. Pat. No. 6,620,570 to Stinson et al. describe a stent delivery catheter having a stent disposed between two tubes where the catheter is fittable through a working channel of an endoscope. Again, the overall profile of the endoscope is limited to a relatively large size as the endoscope must be sized for accenting the stent delivery catheter.

Other approaches include the endoscopic systems as described in U.S. Pat. No. 6,176,873 to Ouchi and U.S. Pat. No. 6,146,389 to Geitz, and International PCT Patent Application Publication No. WO 2005/122953 A2 to Selden. Ouchi describes an endoscope having a mesh stent disposed within the endoscope. The stent has includes rings or tubes at both ends of the stent where the rings or tubes restrict the diameter of the stent ends. A pusher tube within the endoscope is described as being pushed to engage the ring or tube at the distal end of the stent to radially contract the stent and to urge the contracted stent out from a working channel of the endoscope. Such a system makes stent placement difficult as the stent is pushed away from the distal end of the endoscope. Further, the need of rings or tubes at the ends of the stent which are smaller in diameter than the diameter of the expanded stent, limits the use of such a stent as the smaller ends of the stent will tend to restrict flow through the stent. Geitz describes an endoscope having a distal cap. A stent may be disposed over the distal cap and held there via an overlying sheath. For delivery the sheath is removed to deploy the stent. Selden describes a stent radially compressed against the sidewall of the distal portion of an endoscope. The stent is pushed out of the endoscope by a slidable release disposed within the endoscope that engages over the proximal end of the stent. The stent of Seldon is a highly flared stent with outwardly flared ends. Again the pushing of the stent out of the endoscope is problematic as accurate stent placement is difficult. Further, the device of Seldon is apparently limited to a particular stent design, i.e., a highly flared configuration with only the very terminal end portions of the stent being engageable with the wall to the endoscope such that the longitudinal expanse of the stent does not engage the wall of the endoscope as the stent is being pushed out of the endoscope.

Thus, despite the efforts of the prior art, there is a need for an improved endoscopic stent delivery system. In particular, there is a need for an endoscopic stent delivery system which allows for accurate placement and delivery of the stent and which is not limited or constrained to particular stent designs or sizes as with the prior art devices.

SUMMARY OF THE INVENTION

In one aspect, the present invention is directed to an endoscopic stent delivery device. The device may include an endoscope having an elongate shaft, which includes a proximal end, a distal end, an outer wall and a longitudinal working channel through the elongate shaft defining an inner wall of the elongate shaft; a stent juxtaposingly disposed to a distal portion of the inner wall; and an inner tubular member slidably disposed within the working channel and having a stent holding member engaging an interior portion of the stent for releasably securing the stent to the distal portion of the inner wall. The device may further include a viewing device disposed at the distal end of the endoscope and/or an illuminating device disposed at the distal end of the endoscope.

The device, in particular the inner tubular member, may further include inner and outer telescoping members, where the stent may be disposed over the inner telescoping member. The outer telescoping member has a larger outer diameter than an outer diameter of the inner telescoping member, where exterior wall portions of the outer telescoping member juxtaposing may abut the inner wall of the elongate shaft. Further, the stent may be a radially distensible stent having a radially contracted state and a larger radially expanded state, and the outer telescoping member may abut a proximal end of the stent in the radially contracted state of the stent.

The device may further include a suture thread having a portion securably attached to a proximal portion of the stent. The inner tubular member may farther include a longitudinally extending channel, and the suture thread may longitudinally extend through the longitudinal channel of the inner tubular member, whereby a pulling force proximally applied on the suture thread extending through the inner member may proximally move the stent within the working channel. The device may further include a stent loading member for radially compressing the stent into the working channel.

Packaging, kits and methods of use are also provided

DETAILED DESCRIPTION OF THE INVENTION

The present invention relates to an endoscopic assembly and method for transporting and deploying a stent or other intraluminary member, as described herein, in a bodily passageway. The assembly is useful for medical applications in, but not limited to, the gastrointestinal tract, the biliary, tract, the urinary tract, and the respiratory tract. In particular, a preferred embodiment of the present invention is directed to an endoscopic delivery system having a stent loaded into a working channel. The stent may be loaded into the working channel of the endoscope either by a manufacturer of the assembly or by a practitioner of the assembly prior to use. The endoscope may be a disposable endoscope or a non-disposable endoscope. The endoscopic assembly and method of the present invention is particularly suitable for delivering a self-expanding esophageal stent. The endoscopic assembly in accordance with the present invention, however, could also be used in the neurological system (e.g., in the brain), the vascular system (e.g., in arteries or veins), in the cardiovascular system (e.g., in the heart) and in the like. Reference to bodily passageways may be to passageways in any of the aforementioned tracts and systems or elsewhere in the body.

References herein to the term "distal" and variants thereof refer to a direction away from an operator of the subject invention, while references to the term "proximal" and variants thereof refer to a direction towards the operator of the subject invention. Accordingly, when the terms "distal" and "proximal" are used herein in the context of an assembly device that is being deployed within a body, such as a human body, by an operator, the term "distal" refers to a location within or near the body that is further within the body than a location that is "proximal" to the operator.

Figures 1, 2:
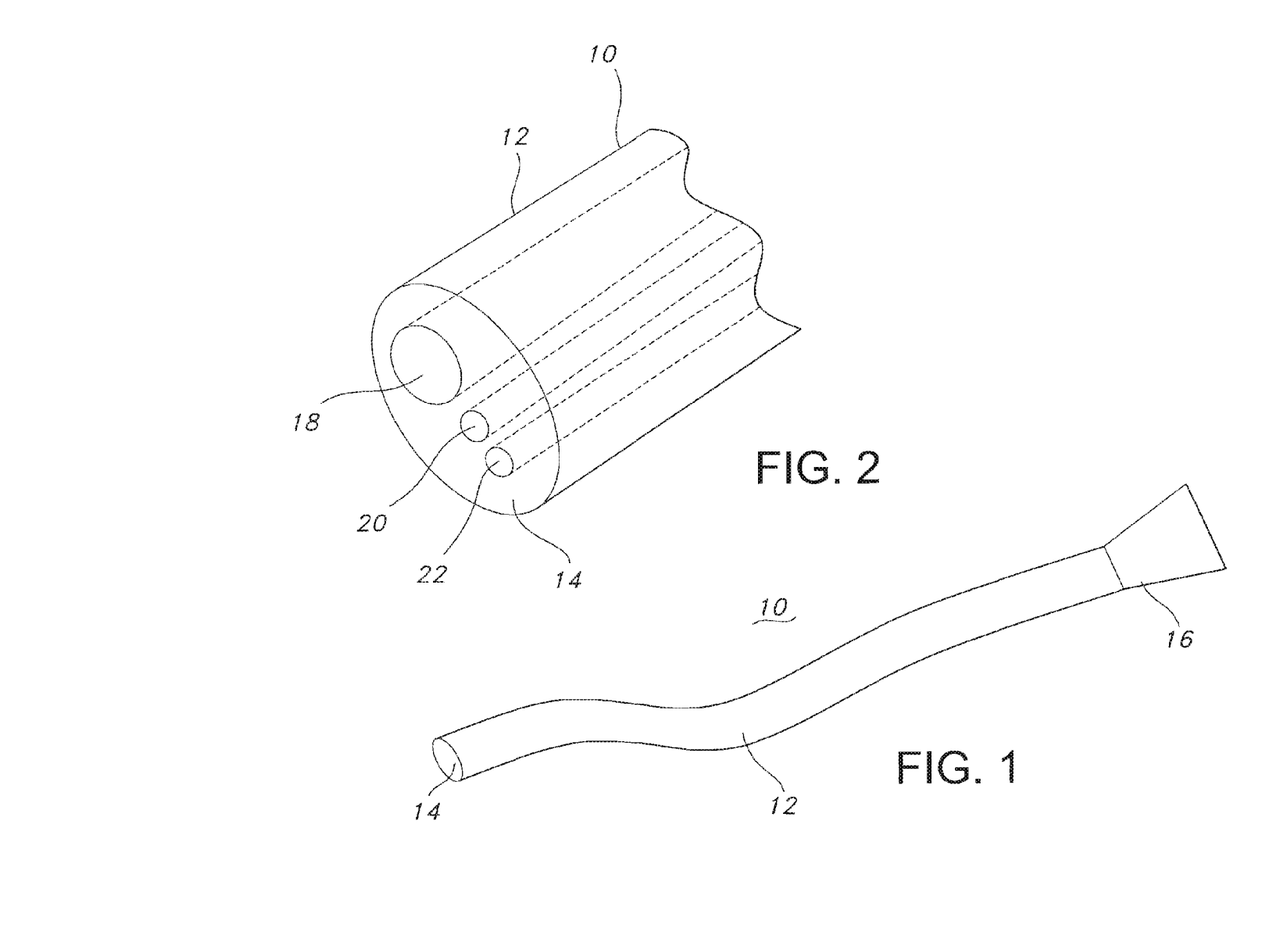
FIG. 1 is a perspective view of an embodiment of an endoscopic stent delivery device or system of the present invention.
FIG. 2 is an exploded or enlarged view of the distal end of the endoscopic stent delivery device or system of FIG. 1.

FIG. 1 is a perspective view of an endoscopic stent delivery system or device 10 according to the present invention. The endoscopic system 10 is particularly well suited for the transluminal delivery and intraluminal deployment of a radially self-expanding prosthesis, such as a stent and/or a stent-graft. The endoscopic system 10 includes an elongate, flexible tubular member 12. The endoscopic system 10 also includes a distal end 14 suitable for intraluminal navigation within bodily lumens (not shown). The proximal end 16 is not intended for placement within a bodily lumen and suitably has controls, devices and/or connections (not shown) for visualization and delivery of a stent (not shown) contained or preloaded in the system 10. Such controls or devices may include, but are not limited to, stent delivery controls, system steering controls, controls for a source of gas or liquid, such as a flushing fluid for aiding endoscopic viewing, aids for viewing or illuminating, and the like.

FIG. 2 is an exploded or expanded view of the distal end 14 of the system 10 of the present invention. As depicted in FIG. 2, the tubular member 12 of the endoscopic system 10 includes a working channel 18, an illumination device or channel 20 and a visualization device or channel 22. The working channel 18 is useful for containing a radially contracted stent (not shown) and for delivery of the stent into a bodily lumen. While the illumination channel 20 and the visualization channel 22 are depicted as two separate channels, the present invention is not so limited. For example, illumination and visualization functions may be combined into a single channel or otherwise provided within or about the flexible tubular member 12.

The illumination device or channel 20 provides light for the operation of the endoscope 10 within a bodily lumen. The illumination channel or channel 20 may include, but is not limited to, a light emitting diode or a number of light emitting diodes, a fiber optic illumination guide for providing light from a light source, such as a laser or a white light source, and the like. Further a lens (not shown) may also be provided at the distal end of illumination channel or channel 20 to focus the illumination on the bodily lumen or tissue. The visualization device or channel 22 may be used to optically or electrically transmit images through the flexible tubular member 12 of the system 10 of the present invention. The visualization device or channel 22 may include, but is not limited to, an objective lens and fiber optic imaging light guide communicating with a practitioner, a camera, a video display, a cathode ray tube (CRT), a liquid crystal display (LCD), digital light processing (DLP) panel, a plasma display panel (PDP), a light-emitting diode (LED) display, an organic light-emitting diode (OLED) display, a sensor, such as a charge-coupled device (CCD) sensor or a complementary metal oxide semiconductor (CMOS) sensor, and the like for use with computer displays, video monitors, televisions and the like.

Figure 3:
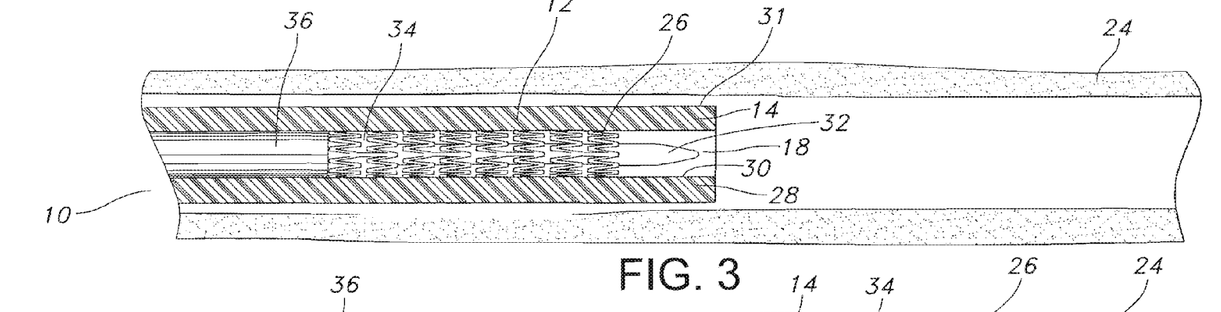
FIG. 3 is a cross-section view of the endoscopic stent delivery device or system of FIG. 1 having a radially contracted stent disposed with the device or system.

The endoscopic system 10 of the present invention is depicted in a partial cross-sectional view in FIG. 3. As depicted in FIG. 3 the distal portion 14 of the flexible tube 12 is positioned within a bodily lumen 24. A stent 26 is contained within the working channel 18 at the distal portion 14 of the endoscopic delivery system 10. The working channel 18 is an elongate cavity, desirably a tubular cavity, extending through the flexible tube 12. The working channel 18 also defines a wall portion 28 of the flexible tube 12 or working channel 18. The stent 26 is disposed against the inner wall surface 30 of the working channel 18 of the flexible member 12.

Figure 4:
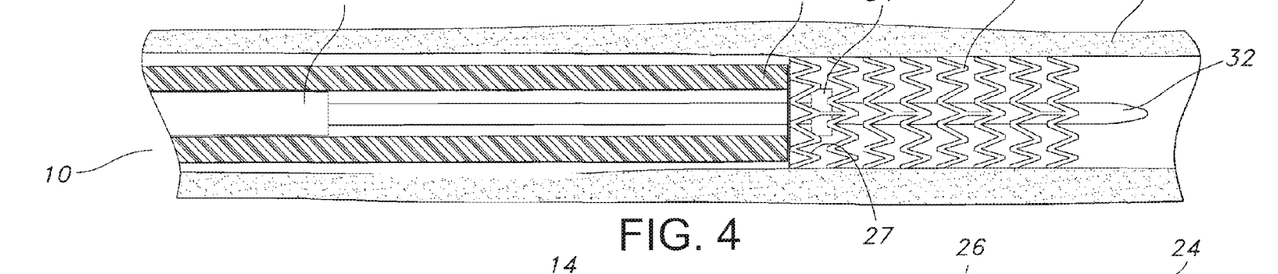
FIG. 4 is a cross-section view of the endoscopic stent delivery device or system of FIG. 3 illustrating the initial deployment of a stent within a bodily lumen.
Figure 5:
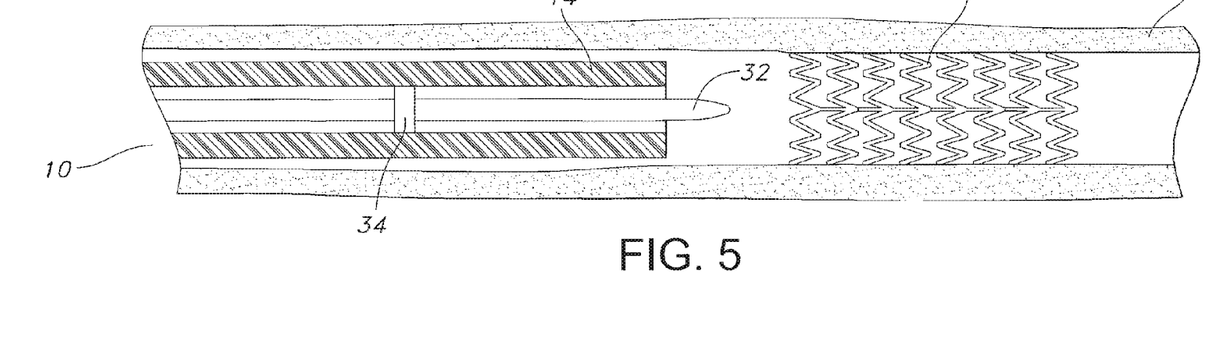
FIG. 5 is a cross-section view of the endoscopic stent delivery device or system of FIG. 3 illustrating the full or complete deployment of a stent within a bodily lumen.

In FIG. 4, the stent 26 is shown as being deployed within the bodily lumen 24. As depicted in FIG. 5, after the stent is deployed within the bodily lumen 24 the endoscopic delivery device may be retracted or withdrawn from the bodily lumen 24. Further, as depicted in FIGS. 3-5, the endoscopic system 10 further includes an inner tubular member 32 having a stent holding member 34. The stent holder 34 releasably secures the stent 26 between the inner tubular member 32 and the inner wall surface 30 of the working channel 18. Desirably, the stent holder 34 is a hollow tubular band. More desirably, the stent holder 34 is a hollow tubular band that is free or substantially free of barbs, pins or protrusions which may engage and possible damage the stent 26. The stent holder 34 may be made of any suitable polymeric, rubber, ceramic or metallic material. Moreover, the stent holder 34 may have a pattern, such as a surface pattern of indentations and/or protrusions, for facilitating securement of the stent 26. In some embodiments, the stent holder 34 may have barbs, pins, fins or protrusions which may engage the stent 26, in particular interior portions 27, 63, 65 of the stent 26, 60. Such interior portions 27, 63, 65 of the stent 26, 60 may include interstitial portions 27, 63, such as an interstitial portions 27 between undulation portions of the stent 26 (see, e.g., FIG. 4) or an interstitial portions 63 between braided filaments 62 of the stent 60 (see, e.g., FIG. 14). Further, the interior portions 27, 63, 65 of the stent 26, 60 may include the interior or luminal surface 65 of the stent 26, 60 (see, e.g., FIG. 15). Moreover, with any of the embodiments, the device or system 10 may include multiple stent holders 34, either axially spaced apart or axially juxtaposed. Further, the stent holder 34 may not have to completely encompass the inner tubular member 32, but may be only partially disposed around a circumferential portion of the inner tubular member 32. Desirably, stent holder 34 is disposed to secure a proximal portion of the stent 26.

The endoscopic system 10 of the present invention may further, and optionally, include an intermediate tubular member 36. As described further below, the intermediate tubular member 36 may be useful for loading the stent 26 within the working channel 18 by, for example, a practitioner or user, where the stent 26 has not been preloaded into the working channel 18 by, for example, the manufacturer of the endoscopic system 10. Additionally, as described below, the intermediate tubular member 36 may also be useful for deploying, repositioning and/or retrieving the stent 26.

Figures 6, 7:
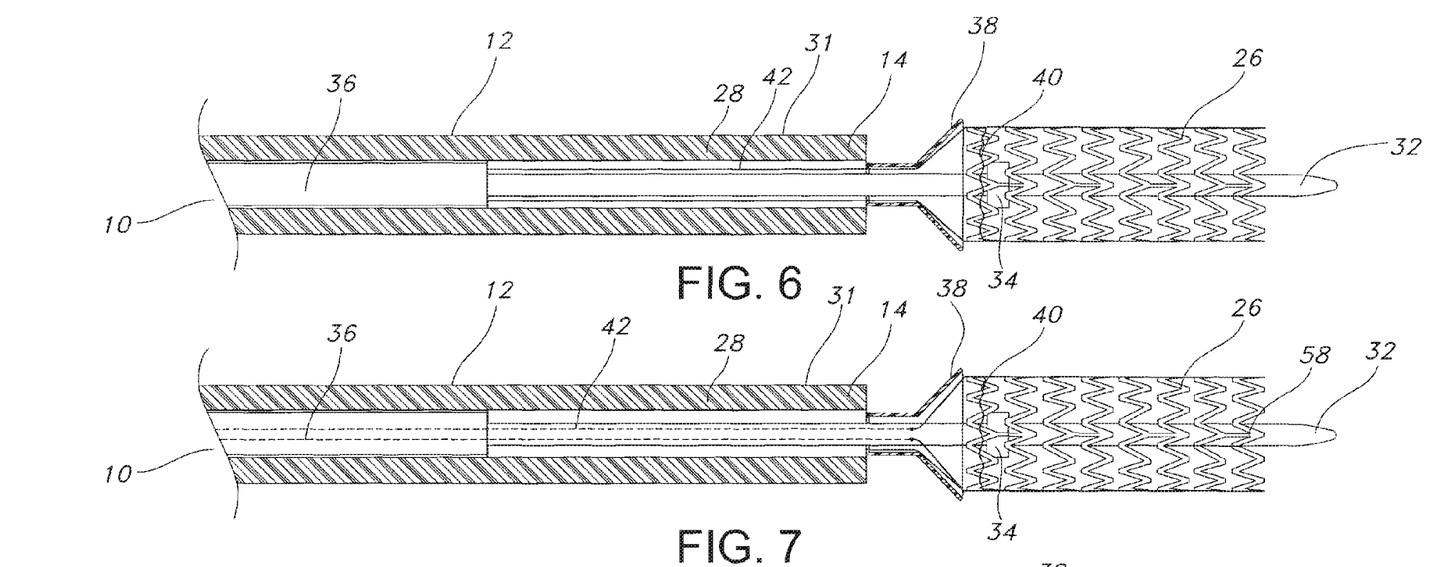
FIG. 6 is a cross-section view of the endoscopic stent delivery device or system of FIG. 1 depicting a stent prior to being disposed within the device or system and having a suture thread secured to the proximal end of the stent with the suture thread being disposed over an inner tubular member.
FIG. 7 is a cross-section view of the endoscopic stent delivery device or system of FIG. 1 depicting a stent prior to being disposed within the device or system and having a suture thread secured to the proximal end of the stent with the suture thread being disposed within an inner tubular member.
Figure 8:
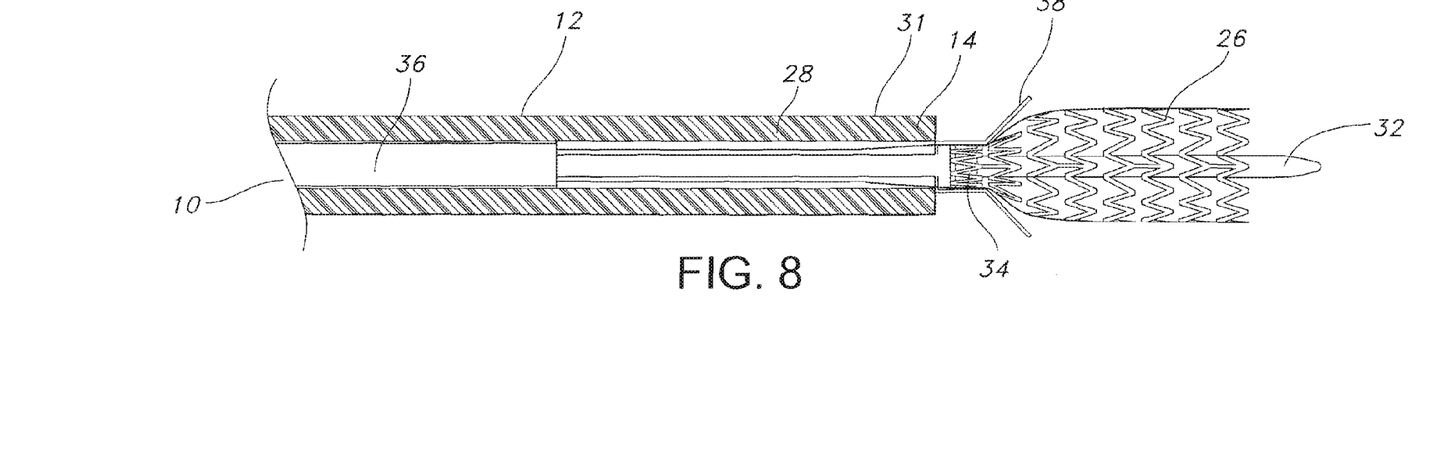
FIG. 8 is a cross-section view of the endoscopic stent delivery device or system of FIG. 6 depicting the initial loading of the stent to within the device or system of FIG. 1.

FIGS. 6-10 depict several embodiments which may allow a practitioner or user to load the stent 26 within the working channel 18 of the endoscopic system 10. As depicted in FIGS. 6-8, a stent engaging member 38, which is depicted as being in the shape of a funnel, may be provided. In one aspect of the present invention, the stent engaging member 38 is provided separately from the stent 26 and the endoscopic system 10. In other words, the stent engaging member 38 need not be securably attached to the proximal end 14 of the endoscopic system 10. Desirably, the engaging member 38 has a truncated-conical shape, outwardly diverging in the distal direction from its proximal end, e.g., the proximal end being smaller than the distal end. The proximal end has a diameter equal or substantially equal, including slightly larger, to the diameter of the intermediate tubular member 36, but less than the diameter of the wall portion 28 of the flexible tube 12 or working channel 18. The engaging member 38 may be of any reasonable length and/or diameter to permit the loading of the stent 26.

As depicted in FIG. 6, the proximal end of the stent 26 may be placed within the stent engaging member 38. The stent 26 may be squeezed or radially contacted within the stent engaging member 38 for placement against the proximal portion of the wall portion 28 of the working channel 18. A suture loop 40 and thread portions 42 arrangement may be used to facilitate the loading of the stent 26 through within the stent engaging member 38 and into proximal portion of the wall portion 28 of the working channel 18. The thread 42 may be looped radially around the proximal end or a portion of the proximal end of the stent 26 to form a suture loop 40 thereat. The thread portions 42 may be pulled axially away from the stent engaging member 38 and the distal portion 14 of the endoscopic system 10 and toward the proximal end 16 of the endoscopic system 10. Such a pulling force urges the stent 26 within the stent engaging member 38 and radially contracts the stent 26 as it passes through the smaller proximal portion of the stent engaging member 38 as depicted in FIG. 8. In one aspect of the present invention, as depicted in FIGS. 6 and 8, the thread portions 42 may be disposed about or outside of the inner tubular member 32. In another aspect of the present invention, as depicted in FIG. 7, the thread portions 42 may be disposed within the inner tubular member 32.

Figure 9:
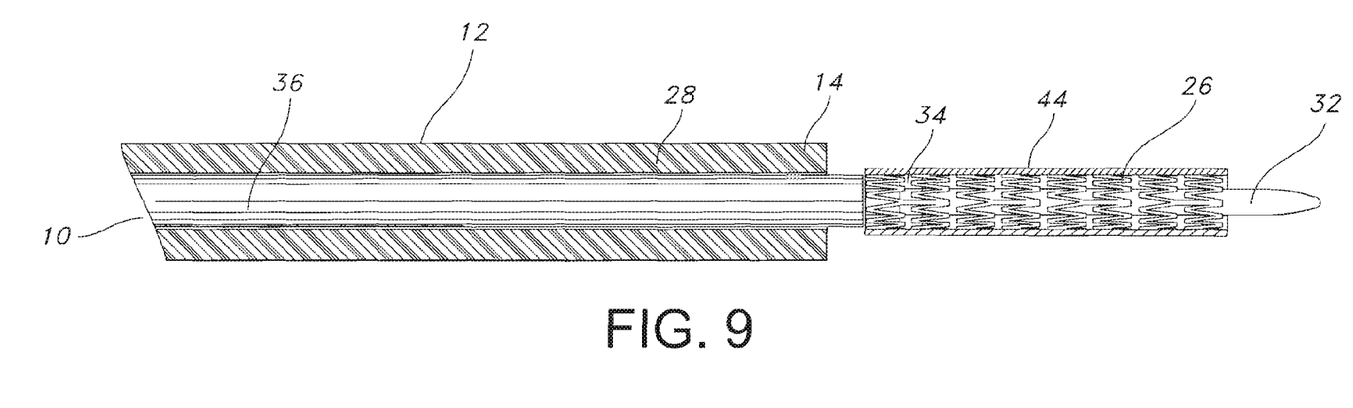
FIG. 9 is an alternate embodiment of the device or system of FIG. 1 showing a radially compressed stent disposed within a stent holding member.

Moreover, as depicted in FIG. 9, the stent 26 may be disposed in a radially contracted state in a stent holding member 44. In such a case, the radially contracted or compressed stent 26 may be slid into the working channel 18 by any of the above described techniques. For example, the practitioner or user may simply push the stent to within the distal portion 14 of the working channel 18 and/or the stent 26 may have a suture loop 40 (not shown) and be pulled by thread portions 42 (not shown).

Figure 10:
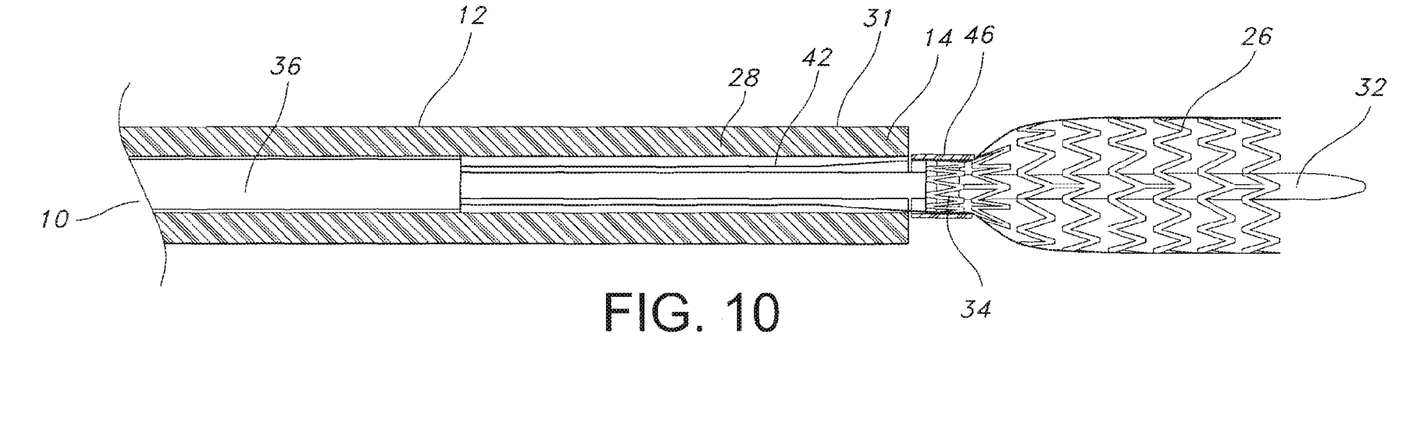
FIG. 10 is an alternate embodiment of the stent holding member of FIG. 9.

Further, as depicted in FIG. 10, a stent engaging member 46 need not have a funnel shape as depicted for the stent engaging member 38 of FIGS. 6-8. As depicted in FIG. 10, the practitioner or used may radially contract or compress only a portion of the stent 26 within the stent engaging member 46, and the stent 26 may then be suitably pulled or pushed or otherwise disposed within the distal portion 14 of the working channel 18.

Alternatively, the stent 26 may be disposed within a loading cartridge (not shown) for facilitating storage and delivery of the stent 26 into the working channel 18. The stent 26 may suitably be loaded in its radially contracted or radially expanded or quiescent state. Desirably, when the stent 26 is a polymeric stent, the stent is stored in the expanded or quiescent state within a loading cartridge or other holding device (not shown). In such a case the stent may be slightly contracted, i.e., less than about five percent radial contraction, so that the stent does not slip or substantially move during transport of handling of the stent holder or stent loading cartridge. The loading cartridge may contain a piston or other axially movable member to facilitate stent movement. Details of suitable stent loading cartridges are further described in U.S. Pat. No. 6,068,635 and/or U.S. Patent Application Publication 2003/0083730 A1, the contents of which are incorporated herein by reference.

Figure 11:
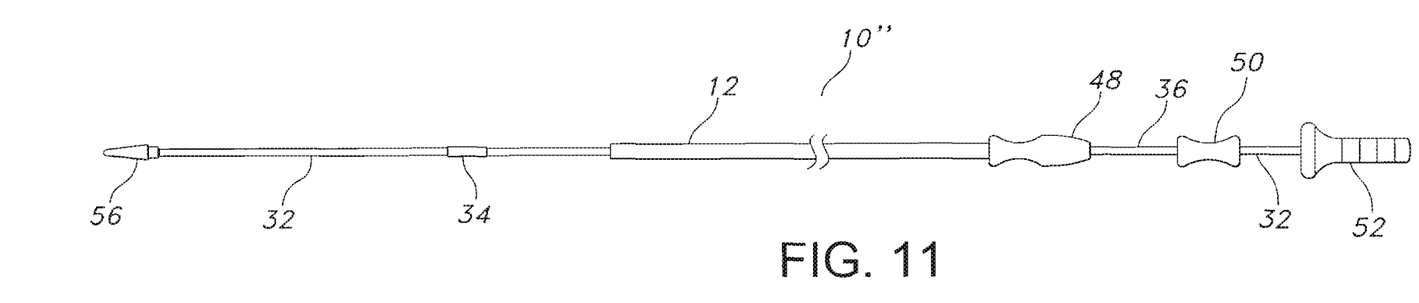
FIG. 11 is a planar view of the endoscopic device or system of FIG. 1.

As discussed above, the endoscopic system 10 of the present invention may optionally include the intermediate tubular member 36. For example, as depicted in FIG. 11, the endoscopic system 10' includes the outer flexible tubular or endoscopic member 12, the intermediate tubular member 36, and the inner tubular member 32. The outer flexible tubular or endoscopic member 12 includes the above-described working channel 18, the illumination device or channel 20 and the visualization device or channel 22. The intermediate tubular member 36 and the inner tubular member 32 are slidably disposed within the working channel 18 of the outer flexible tubular or endoscopic member 12.

The flexible tubular endoscopic member 12, the intermediate tubular member 36, and the inner tubular member 32 may also have respective handles 48, 50, 52 to allow the practitioner or user to control the movement of each member. The handles 48, 50, 52 may be moved or manipulated independently of each other or in concert as a pair while keeping the third or non-paired handle fixed or relatively fixed to allow concurrent movement of two tubular members while keeping the third tubular member fixed or relatively fixed. Further, the handles 48, 50, 52 may be lockable and/or unlockable in unison or in any combination of the handles 48, 50, 52. Moreover, the handles 48, 50, 52 of the endoscopic system 10' may be activated by sliding a button (not shown) on one of the handles or otherwise disposed on the endoscopic system 10'. Such activation may move any or all of the tubular members 12, 36, 32 and/or handles 48, 50, 52.

Furthermore, as depicted in FIG. 11, the systems of the present invention may further include a distal tin 56 disposed at the distal end of the inner tubular member 32. The distal tip 56 is useful for navigating bodily lumens without causing trauma to the same. The stent 26 (not shown) may be preloaded in the system 10' or may be loaded into the system 10' by the practitioner or user. In one aspect of the present invention, the stent 26 is loaded or loadable within the intermediate tubular member 36, and the intermediate tubular member 36 is slid off of the stent 26 to dispose the stent against the wall portion 28 of the working channel 18.

Figure 12:
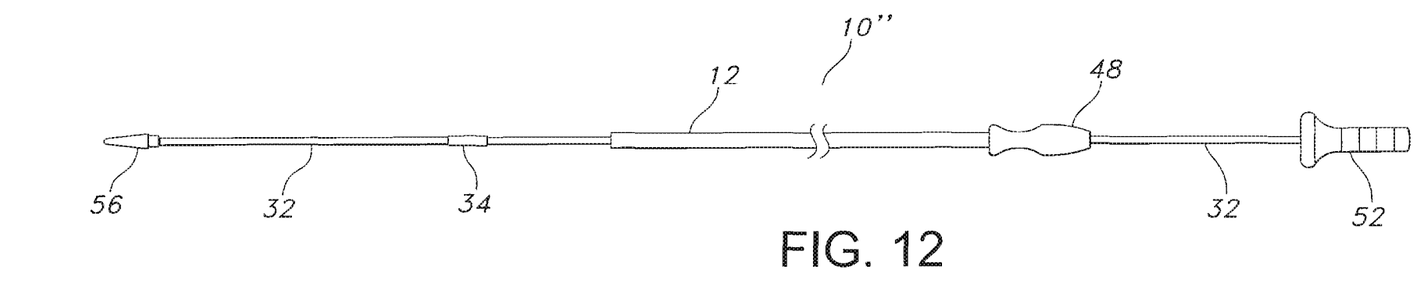
FIG. 12 is a planar view of an alternate embodiment of the endoscopic device or system of FIG. 1.

FIG. 12 depicts the endoscopic system 10" which may not include the intermediate tubular member 36. In such a case the stent 26 (not shown) is normally preloaded into the system 10") but the invention is not so limited. For example, as described above, the stent may be disposed directly against the wall portion 28 of the working channel 18. The endoscopic system 10" includes the above-described outer flexible tubular or endoscopic member 12, including the above-described working channel 18, the illumination device or channel 20 and the visualization device or channel 22.

Figure 13:
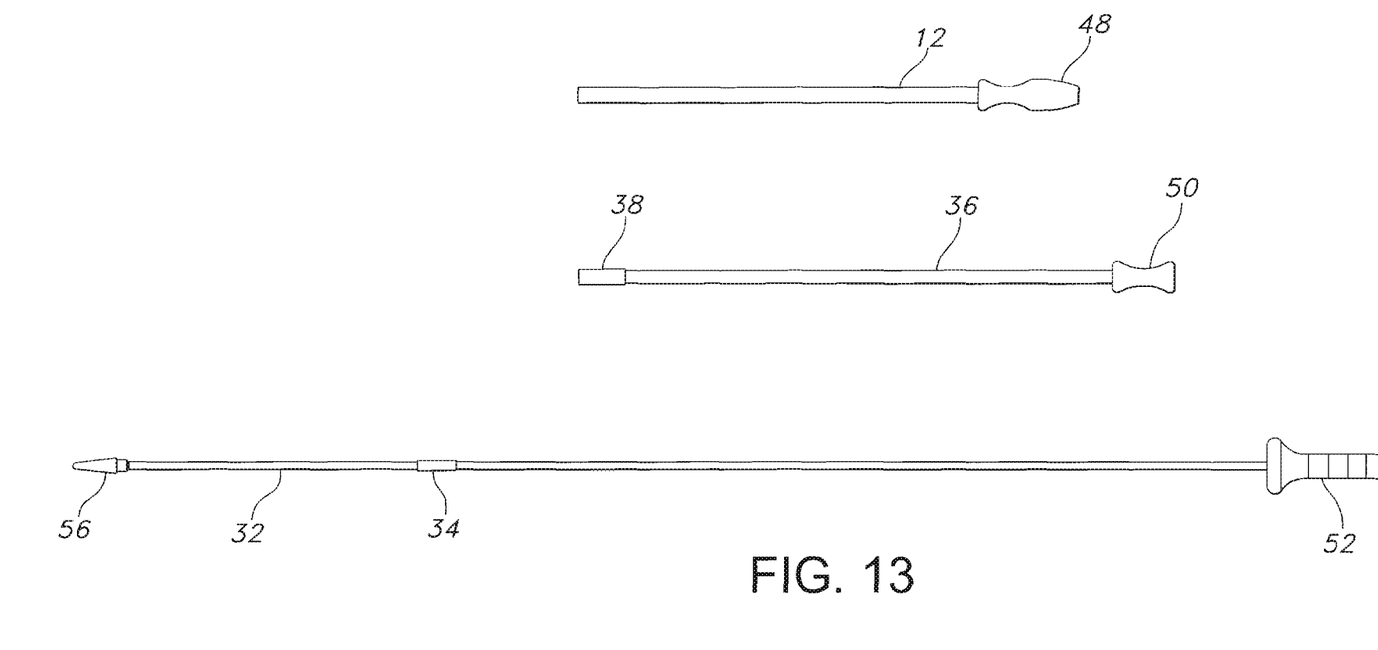
FIG. 13 is a top planar view of different elements of the device or system of FIG. 11 in a dissembled configuration.

FIG. 13 is a top planar view of the different elements of the system 10, 10', 10" of the present invention in an "unassembled" stage. The inner tubular member 32 may be the longest member. The intermediate tubular member 36 may be smaller than the inner tubular member 32, but longer than the outer endoscopic member 12. Finally, the outer endoscopic member 12 may be the shortest of the members. The present invention, however, is not so limited and other tube length configurations may suitably be selected.

The tubular members 12, 32, 36 are formed of a body compatible material. Desirably, the biocompatible material is a biocompatible polymer. Examples of suitable biocompatible polymers include, but are not limited to, polyolefins such as polyethylene (PE), high density polyethylene (HDPE) and polypropylene (PP), polyolefin copolymers and terpolymers, polytetrafluoroethylene (PTFE), polyethylene terephthalate (PET), polyesters, polyamides, polyurethanes, polyurethaneureas, polypropylene and, polycarbonates, polyvinyl acetate, thermoplastic elastomers including polyether-polyester block copolymers and polyamide/polyether/polyesters elastomers, polyvinyl chloride, polystyrene, polyacrylate, polymethacrylate, polyacrylonitrile, polyacrylamide, silicone resins, combinations and copolymers thereof, and the like. Desirably, the biocompatible polymers include polypropylene (PP), polytetrafluoroethylene (PTFE), polyethylene terephthalate (PET), high density polyethylene (HDPE), combinations and copolymers thereof, and the like. Materials for the tubular members 12, 32, 36 may be the same or different.

The tubular members 12, 32, 36, may also have a surface treatment and/or coating on their inner surface, outer surface or portions thereof. A coating need not be applied to all of the tubular members 12, 32, 36, and individual members may be coated, uncoated, partially coated, and the like. Useful coating materials include any suitable biocompatible coating. Non-limiting examples of suitable coatings include polytetrafluoroethylene, silicone, hydrophilic materials, hydrogels, and the like. Useful hydrophilic coating materials include, but are not limited to, alkylene glycols, alkoxy polyalkylene glycols such as methoxypolyethylene oxide, polyoxyalkylene glycols such as polyethylene oxide, polyethylene oxide/polypropylene oxide copolymers, polyalkylene oxide-modified polydimethylsiloxanes, polyphosphazenes, poly(2-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) homopolymers and copolymers of vinyl pyrrolidone, poly (vinylsulfonic acid), acryl amides including poly(N-alkylacrylamide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth)acrylates; polyacrylic acids; polyacrylamides; polyethylene maleic anhydride, combinations and copolymers thereof, and the like. Additional details of suitable coating materials and methods of coating medical devices with the same may be found in U.S. Pat. Nos. 6,447, 835 and 6,890,348, the contents of which are incorporated herein by reference. Such coatings and/or surface treatment is desirably disposed on the inside or a portion thereof of the outer tubular member 12 to aid, if desired, in loading and/or deploying of the stent 26. Further, the outer tubular member 12, and/or other tubular members 32, 36, may also have see-through portions to aid the stent delivery procedure. Such portions may be transparent, substantially transparent, translucent, substantially translucent and the like. Additional details of delivery devices having such transparent and or translucent portions may be found in U.S. Patent Application Publication No. 2003/0050686 A1 to Raeder-Devens et al., the contents of which are incorporated herein by reference.

Figure 14:
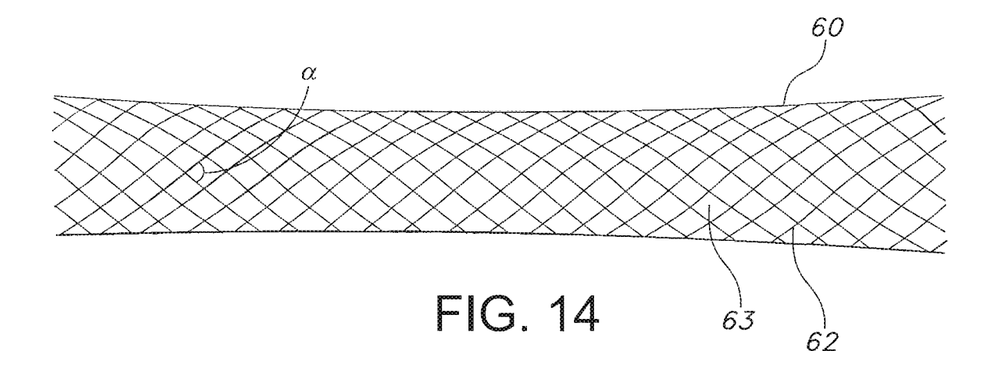
FIG. 14 is an exploded or enlarged view of a braided stent according to one aspect of the present invention.

Any stent that is capable of radial expansion may be used in accordance with the present invention. For example, a radially distensible stent 26 which does not substantially longitudinally elongate upon radial contraction is useful. A non-limiting example of such a stent 26 is one formed from zig-zag or undulating wires or wire as depicted in FIGS. 3-10. One undulating or zig-zag wire may be joined another undulating or zig-zag wire by, for example, a wire strut 58. Alternatively, as depicted in FIG. 14, a stent 60, which is capable of being radially compressed and longitudinally extended for implantation into a bodily lumen, may be suitably used. The degree of elongation depends upon the structure and materials of the stent 60 and may be quite varied. The diameter of the stent 60 also may become several times smaller as it elongates. It is preferred that the stent 60 be constructed to self-expand when released from a radially compressed state. Thus, various stent types and stent constructions may be employed in the invention, and the invention can be constructed to accommodate stents of various sizes and configurations.

As depicted in FIG. 14, one embodiment of the present invention applies the method and system of the present invention to a braided stent 60. FIG. 14 is an exploded or enlarged view of the stent 60 to depict the braiding of the stent filaments 62. As used herein the term braiding and its variants refer to the diagonal intersection of elongate filaments 62 so that each filament passes alternately over and under one or more of the other filaments, which is commonly referred to as an intersection repeat pattern. Useful braiding patterns include, but are not limited to, a diamond braid having a 1/1 intersection repeat pattern, a regular braid having a 2/2 intersection repeat pattern or a hercules braid having a 3/3 intersection repeat pattern. The passing of the filaments under and over one and the other results in slidable filament crossings that are not interlooped or otherwise mechanically engaged or constrained. The filaments 62 are interbraided at a crossing angle, $\alpha$. The crossing angle, $\alpha$, may be any useful acute or obtuse angle. For example, acute angles from about 10° to about 80°, more desirably from about 35° to about 55°, are useful. Obtuse angles from about 95° to about 170°, more desirably from about 100° to about 120°, are also useful.

The stent 26, 60 may also include inwardly and/or outwardly tapered portions (not shown) and/or inwardly or outwardly flared portions (not shown), such as inwardly or outwardly flared stent end portions. The stent 26, 60 may also be a branched stent (not shown), such as, but not limited to, a bifurcated stent (not shown). The stent 26, 60 may also include apertures and/or discontinuities (not shown) along portions of the stent wall. Furthermore, the ends of the stent 26, 60 may be atraumatic, i.e., ends being free or substantially free of loose wire ends or of other sharp projections.

While the stent 26, 60 may be formed of metals, plastics or other materials, it is preferred that a biocompatible material or construction is employed. Useful biocompatible materials include, but are not limited to, biocompatible metals, biocompatible alloys, biocompatible polymeric materials, including synthetic biocompatible polymeric materials and bioabsorbable or biodegradable polymeric materials, materials made from or derived from natural sources and combinations thereof. Useful biocompatible metals or alloys include, but not limited to, nitinol, stainless steel, cobalt-based alloy such as Elgiloy, platinum, gold, titanium, tantalum, niobium, polymeric materials and combinations thereof. Useful synthetic biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, silks and polytetrafluoroethylenes. The polymeric materials may further include a metallic, a glass, ceramic or carbon constituent or fiber. Useful and nonliming examples of bioabsorbable or biodegradable polymeric materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Further, the stent 26, 60 may include materials made from or derived from natural sources, such as, but not limited to collagen, elastin, glycosaminoglycan, fibronectin and laminin, keratin, alginate, combinations thereof and the like.

Further, the stent 26, 60 may be made from polymeric materials which may also include radiopaque materials, such as metallic-based powders or ceramic-based powders, particulates or pastes which may be incorporated into the polymeric material. For example, the radiopaque material may be blended with the polymer composition from which the polymeric wire is formed, and subsequently fashioned into the stent as described herein. Alternatively, the radiopaque material may be applied to the surface of the metal or polymer stent. Various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent 26, 60 may be selectively made radiopaque at desired areas along the stent or made be fully radiopaque, depending on the desired end-product and application. Further, portions of the stent 26, 60, for example stent filaments, may have an inner core of tantalum, gold, platinum, iridium or combination of thereof and an outer member or layer of nitinol to provide a composite filament for improved radiocapicity or visibility. Alternatively the stent 26, 60 may also have improved external imaging under magnetic resonance imaging (MRI) and/or ultrasonic visualization techniques. MRI is produced by complex interactions of magnetic and radio frequency fields. Materials for enhancing MRI visibility include, but not be limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization the stent 26, 60 of the present invention may include ultrasound resonant material, such as but not limited to gold.

Other features, which may be included with the stent 26, 60 of the present invention, include radiopaque markers: surface modification for ultrasound, cell growth or therapeutic agent deliver; varying stiffness of the stent or stent components; varying geometry, such as tapering, flaring, bifurcation and the like; varying material; varying geometry of stent components, for example tapered stent filaments; and the like. The stent struts or filaments may also have any suitable geometry, such as, but not limited to a round cross-sectional geometry, an elliptical cross-sectional geometry, a flat cross-sectional geometry, a square cross-sectional geometry, a triangular cross-sectional geometry, and the like. Such different geometries may be congruent, i.e., substantially the same, or may be varied, for example, having a varying cross-sectional area, e.g., flared. Further, the stent struts and/or filaments may be multifilament members, where the multiple filaments may be the same or different and include, in any combination, any of the above-described biocompatible materials. Moreover, radiopaque markers may be disposed on the stent and/or components of the stent delivery device.

Figure 15:
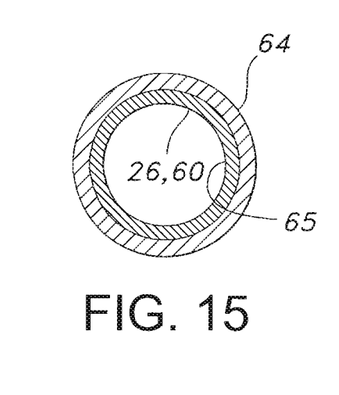
FIG. 15 is a cross-sectional view of a stent of the present invention illustrating an outer graft covering disposed on the stent.
Figure 16:
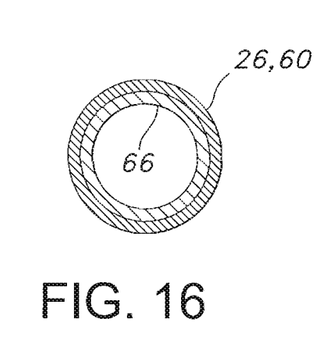
FIG. 16 is a cross-sectional view of a stent of the present invention illustrating an inner graft lining disposed on the stent.
Figure 17:
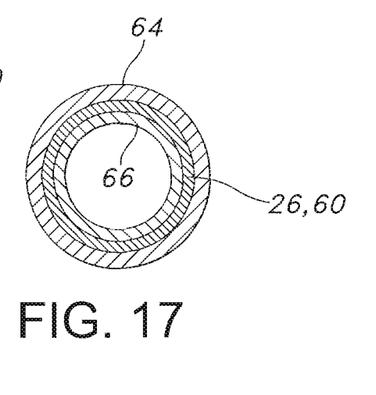
FIG. 17 is a cross-sectional view of the stent of the present invention illustrating an inner graft lining and an outer graft covering disposed on the stent.

Also, the stent 26, 60 may have coverings, films, coatings, and the like disposed over, under or throughout or embedding the stent 26, 60. For example, as depicted in FIG. 15, the stent 26, 60 may include a covering 64, desirably a polymeric covering, disposed over the longitudinal length or a portion of the longitudinal length of the stent 26, 60. Further, as depicted in FIG. 16, the stent 26, 60 may include a liner 66, desirably a polymeric liner, disposed within the longitudinal length or a portion of the longitudinal length of the stent 26, 60. Moreover, as depicted in FIG. 17, the stent 26, 60 may include a both a covering 64 and a liner 66, desirably a polymeric covering and liner which include the same or different polymeric materials, disposed over and within the longitudinal length or a portion of the longitudinal length of the stent 26, 60. The covering and the liner of FIG. 17 may be a unitary film or coating that embeds or partially embeds the stent 26, 60. The covering 64 and/or the liner 66 may be in the form of a tubular structure, for example composed of polymeric material and/or silicone. The covering 64 and/or the liner 66 may also comprise any plastic or polymeric material, desirably a somewhat hard but flexible plastic or polymeric material. The covering 64 and/or the liner 66 may be transparent or translucent, desirably substantially or partially transparent. Furthermore, the covering 64 and/or the liner 66 may be constructed of any suitable biocompatible materials, such as, but not limited to, polymers and polymeric materials, including fillers such as metals, carbon fibers, glass fibers or ceramics. Useful covering 64 and/or the liner 66 materials include, but are not limited, polyethylene, polypropylene, polyvinyl chloride, polytetrafluoroethylene (PTFE), including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, silicones, and copolymers and combinations thereof. The coating or coatings may be on the stent 26, 60, components of the stent 26, 60, and combinations thereof. The stent components, in part or in total, may be temporary, for example bioabsorbable, biodegradable, and the like, or may be permanent (i.e., not substantially bioabsorbable or biodegradable), for example the above-described biocompatible metals, alloys and polymers.

Moreover, the stent 60 may include braided polyester filaments, such as PET polyester filaments. Further, in some applications, the stent 60 is desirably embedded in a coating of silicone. Additional details of such desirable stents are described in U.S. Pat. No. 6,162,244, the contents of which are incorporated herein by reference.

Further, the stent 26, 60 may be repositionable, removable and/or reconstrainable, and/or may include multiple interconnected or non-interconnected stents. For example, the stent 26, 60 may include a loop or element such as a suture loop or element, a polymeric loop or element, metallic or element, and combinations thereof which may be accessible to a user or practitioner, for example by the use of forceps, to reposition, remove and/or reconstrain the stent 26, 60 after it has been delivered, partially or totally, to a bodily lumen. Moreover, a loop or element may be integrally formed as part of the stent 26, 60. Further details of useful repositioning, removing and/or reconstraining loops or elements may be found in U.S. patent application Ser. No. 11/341,540, filed Jan. 7, 2006 and entitled "Stent Retrieval Member And Devices And Methods For Retrieving Or Repositioning A Stent" and in U.S. patent application Ser. No. 11/432,065, filed May 11, 2006, and entitled "Integrated Stent Repositioning And Retrieval Loop", the contents of both of which are incorporated herein by reference.

Further, the stent 26, 60 may be treated with a therapeutic agent or agents, such as, but not limited to, anti-thrombogenic agents (such as heparin, heparin derivatives, urokinase, and PPack (dextrophenylalanine proline arginine chloromethylketone); anti-proliferative agents (such as enoxaparin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Figure 18:
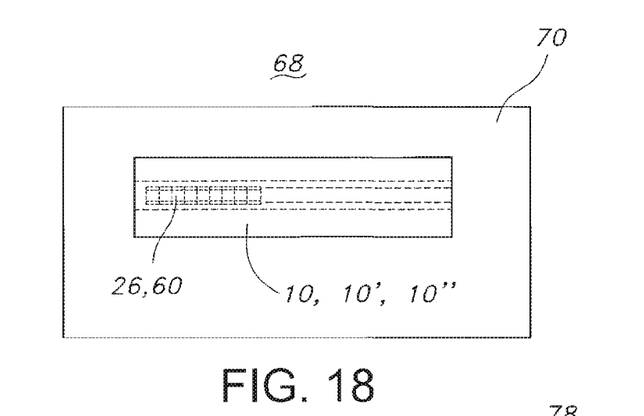
FIGS. 18-21 depict kits including the endoscopic device or system of FIG. 1.
Figure 19:
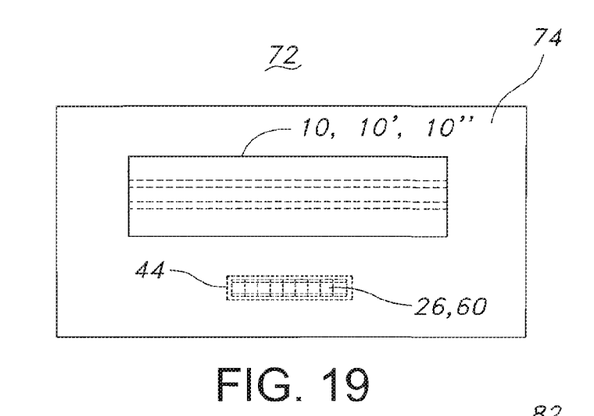
Figure 20:
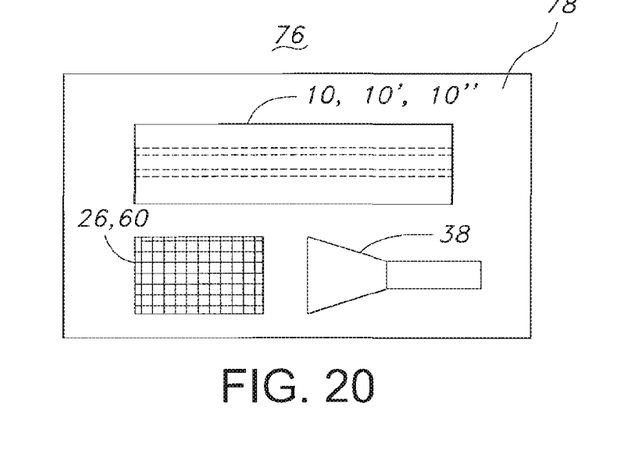
Figure 21:
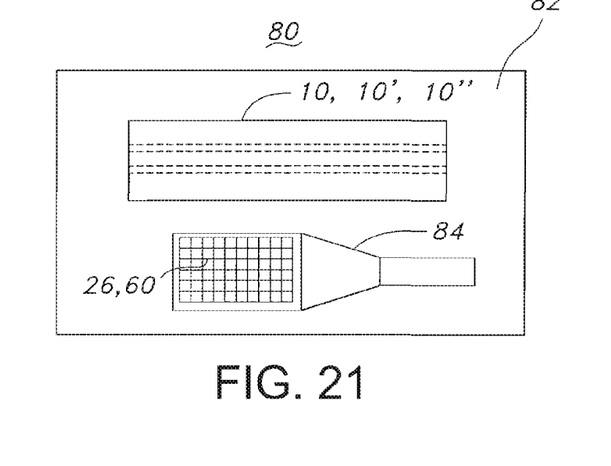

The systems 10, 10', 10" of the present invention may be provided in or with packaging to contain and/or hermetically seal or contain the systems and devices of the present invention. As depicted in FIG. 18, a kit 68 may include the endoscopic system 10, 10', 10" with a radially contracted or compressed stent 26, 60 there within. The kit may include a packaging 70 to contain or seal, including hermetically, the components therein. As depicted in FIG. 18, a kit 68 may include the endoscopic system 10, 10', 10" with a radially contracted or compressed stent 26, 60 there within. The kit 68 may include a packaging 70 to contain or seal, including hermetically, the components therein. As depicted in FIG. 19, a kit 72 may include the endoscopic system 10, 10', 10" with a radially contracted or compressed stent 26, 60 contained within the stent holding member 44. The kit 72 may include a packaging 74 to contain or seal, including hermetically, the components therein. As depicted in FIG. 20, a kit 76 may include the endoscopic system 10, 10', 10", a non-radially contracted or expanded stent 26, 60 and the stent engaging member 38. The kit 76 may include a packaging 78 to contain or seal, including hermetically, the components therein. As depicted in FIG. 21, a kit 80 may include the endoscopic system 10, 10', 10" and a non-radially contracted or expanded stent 26, 60 contained within a loading cartridge 84, including the above-described loading cartridges. The kit 80 may include a packaging 82 to contain or seal, including hermetically, the components therein.

The present invention, however, is not limited to separately a disposed stent engaging member 38 and/or a loading cartridge 84. For example, the engaging member 38 may be disposed at the distal end of the intermediate tubular member 36. In such a case the intermediate tubular member 36 may be formed of a thin polymeric film, for example, but not limited to, polyamide, such as polyamide 6-6 or nylon, PET or PTFE. The film is desirably compliant, so that the funnel is capable of alternatively assuming an open configuration as seen in FIGS. 6-8 for receiving a proximal end of stent 26, 60, and a collapsed configuration to allow engaging member 38 to be accommodated or contained within the working channel 18 of the flexible tubular endoscopic member 12. Desirably, such an attached engaging member 38 is resilient and tends to assume the open configuration in the relaxed state when free of external stresses. Alternatively, the engaging member 38 may be pliable, in particular radially distensible, mesh, weave or braid. The engaging member 38 may be of any reasonable length and/or diameter to permit the loading of the stent 26, 60. Additional details of such attached engaging members 38 may be in U.S. patent application Ser. No. 11/437,889, entitled "Apparatus And Method For Loading And Delivering A Stent", filed May 19, 2006, the contents of which is incorporated herein by reference. The engaging member 38 may be assembled during operation, for example, two halves of the member 38 may snap or otherwise be engaged around the stent 26, 60, or the member 38 may be made into a funnel shape, for example, a flat sheet of material rolled into a cone shape around the stent 26, 60.

In one aspect of the present invention, an endoscopic stent delivery device 10, 10', 10''' is provided. The device 10, 10', 10''' includes an endoscope 10, 10', 10" comprising an elongate shaft 12 comprising a proximal end 14, a distal end 16, an outer wall portion 31 and a longitudinal working channel 18 through the elongate shaft 12 defining an inner wall 30 of the elongate shaft 12; a stent 26, 60 juxtaposingly disposed to a distal portion 14 of the inner wall 30; and an inner tubular member 32 slidably disposed within the working channel 18 and having a stent holding member 34 engaging an interior portion or portions 27, 63, 65 of the stent 26, 60 for releasably securing the stent 26, 30 to the distal portion 14 of the inner wall 30. The device 10, 10', 10''' may further include a viewing device 22 disposed at the distal end 14 of the endoscope 10, 10', 10" and/or an illuminating device 20 disposed at the distal end 14 of the endoscope 10, 10', 10".

The stent holding member 34 may include a tubular band; where the tubular band may partially or completely encompass a portion of the inner tubular member 32. Further, the stent holding member 34 may include elongate, desirably thin, members, which are sometimes referred to as prongs or whiskers that may engage the portions of the stent 26, 60 within the delivery device 10, 10', 10" of the present invention. Further details of a stent holding member having such elongate members may be found in U.S. Pat. No. 6,656,212 to Ravenscroft et al., the contents of which are incorporated herein by reference.

Desirably, the elongate shaft 12 is proximally slidable for releasing the stent 26, 60 from the working channel 18. The stent 26, 60 may be a radially distensible stent. Such a stent 26, 60 has a radially contracted state and a larger radially expanded state, where the stent 26, 60 is disposed within the working channel 18 in the radially contacted state. The radially distensible stent 26, 60 may be a polymeric stent, a self-expanding stent, a braided stent 60 and/or a zig-zag stent 26 having a plurality of undulating filament portions, or combinations thereof. The zig-zag stent 26 may further include struts 58 for interconnecting one undulating filament portion to another undulating filament portion.

Further, a graft 64, 66 disposed over at least a portion of the stent 26, 60. The graft 64, 66 may be selected from the group consisting of a covering 64, a liner 66, a film, a coating and combinations thereof. Desirably, the stent 60 is a braided polymeric stent and the graft 64, 66 comprises silicone.

Moreover, the inner tubular member 32 may further include inner and outer telescoping members 32, 36, where the stent 26, 60 is disposed over the inner telescoping member 32. The outer telescoping member 36 typically has a larger outer diameter than an outer diameter of the inner telescoping member 32, where exterior wall portions of the outer telescoping member 36 may juxtaposing abut the inner wall 30 of the elongate shaft 12. Further, the outer telescoping member 36 may abut a proximal end of the stent 26, 60 in the radially contracted state of the stent 26, 60.

The device 10, 10', 10" may further include a suture thread 40, 42 having a portion 40 securably attached to a proximal portion of the stent 26, 60, where the inner tubular member 32 further includes a longitudinally extending channel and further where the suture thread 42 longitudinally extends through the longitudinal channel of the inner tubular member 32, whereby a pulling force proximally applied on the suture thread 42 extending through the inner member 32 may proximally move the stent 26, 60 within the working channel 18. The device 10, 10', 10" may further include a stent loading member 38 for radially compressing the stent 26, 60 into the working channel 18.

The device 10, 10', 10" may further include a package 70, 74, 78, 82 for enclosing the device 10, 10', 10" and/or for hermetically sealing the device 10, 10', 10" within the package 70, 74, 78, 82.

In another aspect of the invention, an endoscopic stent delivery kit 68, 72, 76, 80 is provided. The kit 72, 76, 80 may include an endoscope 10, 10', 10" comprising an elongate shaft 12 comprising a proximal end 14, a distal end 16, an outer wall 31 and a longitudinal working channel 18 through the elongate shaft 12 defining an inner wall 30 of the elongate shaft 12: a radially distensible stent 26, 60 having a radially contracted state and a radially expanded state; an inner tubular member 32 slidable disposed within the working channel 28 and having a stent holding member 34 engaging an interior portion or portions 27, 63, 65 of the stent 26, 60 for releasably securing the stent 26, 60 to the distal portion 14 of the inner wall 30; and a stent loading member 38, 44, 84 for loading the stent 26, 60 into a distal portion 14 of the working channel 18. The stent 26, 60 may be in a radially contracted state, where the stent 26, 60 is disposed within the stent loading member 44. Alternatively, the stent 26, 60 may be in the radially expanded state. Further, the radially expanded stent 26, 60 may be disposed within the stent loading member 84. The kit 68, 72, 76, 80 may further include a package 70, 74, 78, 82 for enclosing the device 10, 10', 10" for hermetically sealing the endoscope 10, 10', 10", the stent 26, 60, the inner tubular member 32 and the stent loading member within the package 38, 44, 84.

In another aspect of the invention, a method for delivering a stent 26, 60 into a bodily lumen 24 or a method of use is provided. The method or use includes providing an endoscopic stent delivery device 10, 10', 10", the device 10, 10', 10" includes an endoscope 10, 10', 10" including an elongate shaft 12 having a proximal end 14, a distal end 16, an outer wall 31 and a longitudinal working channel 18 though the elongate shaft 12 defining an inner wall 30 of the elongate shaft 12; a stent 26, 60 juxtaposingly disposed to a distal portion 14 of the inner wall 30; and an inner tubular member 32 slidably disposed within the working channel 18 and having a stent holding member 34 engaging an interior portion or portions 27, 63, 65 of the stent 26, 60 for releasably securing the stent 26, 60 to the distal portion 14 of the inner wall 30; and sliding the elongate shaft 12 relative to the inner tubular member 32 to release the stent 26, 60 from the device 10, 10', 10". The stent 26, 60 may be released from the endoscopic stent delivery device 10, 10', 10" by retracting the elongate shaft 12 to release the stent 26, 60 from the delivery device 10, 10', 10" and/or by advancing the inner tubular member 32 to push the stent 26, 60 out of the delivery device 10, 10', 10'. The step of providing the endoscopic stent delivery device 10, 10', 10" may further include a step of loading the stent 26, 60 within the distal portion 14 of the inner wall 30 of the endoscope 10, 10', 10". The method may further include radially compressing the stent 26, 60 prior to loading the stent 26, 60 within the distal portion 14 of the inner wall 30 of the endoscope 10, 10', 10".

Moreover, some or all of the stent delivery components, such as, but not limited to, the flexible tubular endoscopic member 12, the intermediate tubular member 36, the inner tubular member 32, the stent engaging member 38, the stent holding member 44, and/or the loading cartridge 84, may be mechanically engageable, such as keyed, threaded and/or lockable together, to permit rotation and/or to prevent unwanted misalignment or mispositioning of the stent 20, 26. Furthermore, any of the above-described viewing devices and/or illuminating devices may be disposed on or within or in conjunction with any of the above-described any of the above-described components, for example, tubular members 12, 32, 36, of the endoscope 10, 10', 10". Further, the viewing device and the illuminating device may be disposed on different components of the present invention.

The following embodiments or aspects of the invention may be combined in any fashion and combination and be within the scope of the present invention, as follows:

Embodiment 1.: An endoscopic stent delivery device, comprising: an elongate shaft comprising a proximal end, a distal end, an outer wall and a longitudinal working channel through the elongate shaft defining an inner wall of the elongate shaft; a stent juxtaposingly disposed to a distal portion of the inner wall; and an inner tubular member slidably disposed within the working channel and having a stent holding member engaging an interior portion of the stent for releasably securing the stent to the distal portion of the inner wall.

Embodiment 2.: The device of embodiment 1, further comprising a viewing device disposed at the distal end of the elongate shaft.

Embodiment 3.: The device of embodiment 1, further comprising an illuminating device disposed at the distal end of the elongate shaft.

Embodiment 4.: The device of embodiment 1, wherein the stent holding member comprises a tubular band; wherein the tubular band may partially or completely encompass a portion of the inner tubular member.

Embodiment 5.: The device of embodiment 1, wherein the elongate shaft is slidable for releasing the stent from the working channel.

Embodiment 6.: The device of embodiment 1, wherein the stent is a radially distensible stent.

Embodiment 7.: The device of embodiment 6, wherein the stent has a radially contracted state and a larger radially expanded state, and further wherein the stent is disposed within the working channel in the radially contracted state.

Embodiment 8.: The device of embodiment 6, wherein the radially distensible stent is a polymeric stent.

Embodiment 9.: The device of embodiment 6, wherein the radially distensible stent is a self-expanding stent.

Embodiment 10.: The device of embodiment 1, wherein the stent is a braided stent.

Embodiment 11.: The device of embodiment 1, wherein the stent is a zig-zag stent comprising a plurality of undulating filament portions.

Embodiment 12.: The device of embodiment 11, wherein the stent further comprises struts for interconnecting one undulating filament portion to another undulating filament portion.

Embodiment 13.: The device of embodiment 1, further comprising a graft disposed over at least a portion of the stent.

Embodiment 14.: The device of embodiment 13, wherein the graft is selected from the group consisting of a covering, a liner, a film, a coating and combinations thereof.

Embodiment 15.: The device of embodiment 13, wherein the stent is a braided polymeric stent and the graft comprises silicone.

Embodiment 16.: The device of embodiment 1, wherein the inner tubular member comprises inner and outer telescoping members, and further wherein the stent is disposed over the inner telescoping member.

Embodiment 17.: The device of embodiment 16, wherein the outer telescoping member has a larger outer diameter than an outer diameter of the inner telescoping member, and further wherein exterior wall portions of the outer telescoping member juxtaposing abut the inner wall of the elongate shaft.

Embodiment 18.: The device of embodiment 17, wherein the stent is a radially distensible stent having a radially contracted state and a larger radially expanded state, and further wherein the outer telescoping member abuts a proximal end of the stent in the radially contracted state of the stent.

Embodiment 19.: The device of embodiment 1, further comprising a suture thread having a portion securably attached to a proximal portion of the stent, whereby a pulling force applied on the suture thread moves the stent within the working channel.

Embodiment 20.: The device of embodiment 19, further comprising a stent loading member for radially compressing the stent into the working channel.

Embodiment 21: The device of embodiment 1, further comprising a package for enclosing the device for hermetically sealing the device within the package.

Embodiment 22.: An endoscopic stent delivery kit, comprising: an elongate shaft comprising a proximal end, a distal end, an outer wall and a longitudinal working channel through the elongate shaft defining an inner wall of the elongate shaft; a radially distensible stent having a radially contracted state and a radially expanded state; and an inner tubular member slidable disposed within the working channel and having a stent holding member engaging an interior portion of the stent for releasably securing the stent to the distal portion of the inner wall.

Embodiment 23.: The kit of embodiment 22, further comprising a stent loading member for loading the stent into a distal portion of the working channel.

Embodiment 24.: The kit of embodiment 22, wherein the stent is in the radially contracted state, and further wherein the stent is disposed within the stent loading member.

Embodiment 25: The kit of embodiment 22, wherein the stent is in the radially expanded state, Embodiment 26.: The kit of embodiment 25, wherein the radially expanded stent is disposed within the stent loading member.

Embodiment 27: The kit of embodiment 22, further comprising a package for enclosing the device for hermetically sealing the endoscope, the stent, the inner tubular member and the stent loading member within the package.

Embodiment 28.: A method for delivering a stent into a bodily lumen, comprising (a.) providing an endoscopic stent delivery device, the device comprising: (i.) an elongate shaft comprising a proximal end, a distal end, an outer wall and a longitudinal working channel through the elongate shaft defining an inner wall of the elongate shaft; (ii.) a stent juxtaposingly disposed to a distal portion of the inner wall; and (iii.) an inner tubular member slidably disposed within the working channel and having a stent holding member engaging an interior portion of the stent for releasably securing the stent to the distal portion of the inner wall; and (b.) sliding the elongate shaft relative to the inner tubular member to release the stent from the device, Embodiment 29.: The method of embodiment 28, wherein the step of providing the endoscopic stent delivery device further comprises: loading the stent within the distal portion of the inner wall of the endoscope.

Embodiment 30.: The method of embodiment 29, further comprising: radially compressing the stent prior to loading the stent within the distal portion of the inner wall of the endoscope.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

What is claimed is:

1. An endoscopic stent delivery device, comprising:
an elongate shaft comprising a proximal end, a distal end, an outer wall, a longitudinal working channel through the elongate shaft defining an inner wall of the elongate shaft;
a viewing channel extending through the elongate shaft from said proximal end to said distal end;
a viewing device extending through said viewing channel of the elongate shaft;
a stent having a proximal end and a distal end and an inner surface therebetween, said stent juxtaposingly disposed to a distal portion of the inner wall of the working channel;
an inner tubular member slidably disposed within the working channel and having a stent holding member retaining an interior portion of only the proximal end of the stent for releasably securing the proximal end of said stent to the distal portion of the inner wall, said stent holding member comprises a hollow tubular band at least partially disposed around said inner tubular member, said stent holding member extends between said inner tubular member and said inner surface of said stent, said inner tubular member extends through and protrudes from the stent lumen, wherein said stent is directly secured against said inner wall of said working channel of said shaft by said stent holding member.

2. The device of claim 1, further comprising an illuminating channel extending through said elongate shaft from said proximal end to said distal end, and an illuminating device disposed at a distal end of the illuminating channel.

3. The device of claim 1, wherein the elongate shaft is slidable for releasing the stent from the working channel.

4. The device of claim 1, wherein the stent is a radially distensible stent, and wherein the radially distensible stent has a radially contracted state and a larger radially expanded state, and further wherein the stent is disposed within the working channel in the radially contracted state.

5. The device of claim 4, wherein the radially distensible stent is a polymeric stent.

6. The device of claim 1, wherein the stent is a braided stent.

7. The device of claim 1, wherein the stent is a zig-zag stent comprising a plurality of undulating filament portions.

8. The device of claim 1, further comprising a graft disposed over at least a portion of the stent, wherein the graft is selected from the group consisting of a covering, a liner, a film, a coating and combinations thereof.

9. The device of claim 8, wherein the stent is a braided polymeric stent and the graft comprises silicone.

10. The device of claim 1, wherein the inner tubular member comprises inner and outer telescoping members, and further wherein the stent is disposed over the inner telescoping member.

11. The device of claim 10, wherein the outer telescoping member has a larger outer diameter than an outer diameter of the inner telescoping member, and further wherein exterior wall portions of the outer telescoping member are disposed within the working channel.

12. The device of claim 11, wherein the stent is a radially distensible stent having a radially contracted state and a larger radially expanded state, and further wherein the outer telescoping member abuts a proximal end of the stent in the radially contracted state of the stent.

13. The device of claim 1, further comprising a suture thread looped radially around a proximal portion of the stent, whereby a pulling force applied on the suture thread moves the stent within the working channel.

14. The device of claim 13, further comprising a stent loading member for radially compressing the stent into the working channel.

15. The device of claim 1, further comprising a package for enclosing the device for hermetically sealing the device within the package.

16. The device of claim 1, further comprising multiple stent holding members axially spaced apart along said inner tubular member.

17. An endoscopic stent delivery kit, comprising:
an elongate shaft comprising a proximal end, a distal end, an outer wall a longitudinal working channel through the elongate shaft defining an inner wall of the elongate shaft;
a viewing channel extending through said elongate shaft from said proximal end to said distal end;
a viewing device extending through said viewing channel;
a radially distensible stent having a radially contracted state and a radially expanded state;
an inner tubular member slidably disposed within the working channel and having a stent holding member engaging an interior portion of the stent for releasably securing the stent directly to the distal portion of the inner wall of the working channel, the stent holding member extending between the inner tubular member and the inner surface of the stent; and a stent loading member for loading the stent into a distal portion of the working channel, and said stent loading member having a conical geometry, said stent loading member is unattached to said elongated shaft.

18. The kit of claim 17, said stent loading member is removably attached to distal end of said elongate shaft.

19. The kit of claim 17, further comprising a package for enclosing the device for hermetically sealing the endoscope, the stent, the inner tubular member and the stent loading member within the package.

20. A method for delivering a stent into a bodily lumen, comprising
a. providing an endoscopic stent delivery device, the device comprising:
i.) an elongate shaft comprising a proximal end, a distal end, an outer wall, a longitudinal working channel through the elongate shaft defining an inner wall of the elongate shaft; and a viewing channel extending through said elongate shaft from said proximal end to said distal end;
ii.) a stent juxtaposingly disposed to a distal portion of the inner wall;
iii.) an inner tubular member slidably disposed within the working channel and having a stent holding member engaging an interior portion of a proximal end of the stent for releasably securing only the interior portion of the proximal end of the stent between said stent holding member and said working channel of said shaft and securing said interior portion of the proximal end of the stent to the stent holding member, said stent holding member is a tubular band extending around said inner tubular member wherein said stent is directly secured against said inner wall of said working channel of said shaft by said stent holding member; and
iv.) a viewing device extending through said viewing channel; and
b. sliding the elongate shaft relative to the inner tubular member to release the stent from the device.

21. The method of claim 20, wherein the step of providing the endoscopic stent delivery device further comprises:
loading the stent within the distal portion of the inner wall of the elongate shaft.

22. The method of claim 21, further comprising:
radially compressing the stent prior to loading the stent within the distal portion of the inner wall of the endoscope.

* * * * *